US008565856B2

(12) United States Patent
Hamill et al.

(10) Patent No.: US 8,565,856 B2
(45) Date of Patent: Oct. 22, 2013

(54) ULTRASONIC IMAGER FOR MOTION MEASUREMENT IN MULTI-MODALITY EMISSION IMAGING

(75) Inventors: James J. Hamill, Knoxville, TN (US); Günther Platsch, Röthenbach (DE); Michael E. Casey, Louisville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1174 days.

(21) Appl. No.: 12/125,329

(22) Filed: May 22, 2008

(65) Prior Publication Data

US 2009/0076379 A1    Mar. 19, 2009

Related U.S. Application Data

(60) Provisional application No. 60/973,374, filed on Sep. 18, 2007.

(51) Int. Cl.
*A61B 5/05*    (2006.01)

(52) U.S. Cl.
USPC ............................ 600/424; 600/407; 600/463

(58) Field of Classification Search
None
See application file for complete search history.

(56) References Cited

U.S. PATENT DOCUMENTS

| | | | |
|---|---|---|---|
| 6,261,231 B1 * | 7/2001 | Damphousse et al. | 600/437 |
| 2005/0177044 A1 | 8/2005 | Rubin et al. | |
| 2006/0237652 A1 * | 10/2006 | Kimchy et al. | 250/363.02 |

OTHER PUBLICATIONS

Maurer et al., A Review of Medical Image Registration, Interactive Image-Guided Neurosurgery, pp. 17-44, 1993.*
JJ Hamill et al, Respiratory-gated CT as a tool for the simulation of breathing artifacts in PET and PET/CT, Feb. 2008, Am. Assoc. Phys. Med, pp. 576-585, Med. Phys., vol. 35.
Ralph A Bundschuh et al, Postacquisition Detection of Tumor Motion in the Lung and Upper Abdomen Using List-Mode PET Data: A Feasibility Study, May 2007, The Journal of Nuclear Medicine pp. 758-763, vol. 48.
Sudek A. Nehmeh et al, Deep-Inspiration Breath-Hold PET/CT of the Thorax, Jan. 2007, The Journal of Nuclear Medicine, pp. 22-26, vol. 48.
Axel Martinez-Moller et al, Artifacts from Misaligned CT in Cardiac Perfusion PET/CT Studies: Frequency, Effects, and Potential Solutions, Feb. 2007, The Journal of Nuclear Medicine, pp. 188-193, vol. 48.
Mohammad Dawood et al, Ling Motion Correction on Respiratory Gated 3-D PET/CT Images, IEEE 2006, American Institute of Ultrasound Medicine, pp. 476-485, IEEE Transactions on Medical Imaging, vol. 25.
Srini Tridandapani et al, Echocardiology-Based Selection of Quiescent Heart Phases, American Institute of Ultrasound Medicine 2005, pp. 1519-1526, J. Ultrasound Med., vol. 24.
Nye, et al., "Minimizing Artifacts Resulting from Respiratory and Cardiac Motion by Optimization of the Transmission Scan in Cardiac PET/CT", Med. Phys. 34 (6), Jun. 2007, pp.

* cited by examiner

*Primary Examiner* — Long V. Le
*Assistant Examiner* — Bo J Peng
(74) *Attorney, Agent, or Firm* — Peter Kendall

(57) ABSTRACT

A medical imaging device has an emission tomograph, at least one ultrasonic (US) probe for providing images giving real-time information about the location of the internal organs of a subject, a tracking system for spatially locating the at least one ultrasonic probe in relation to the medical imaging device, and an image processing unit in which the location information obtained by the ultrasonic probe is used for attenuation correction of image information obtained by the emission tomograph.

16 Claims, 8 Drawing Sheets

ULTRASONIC IMAGER FOR MOTION MEASUREMENT IN MULTI-MODALITY EMISSION IMAGING

CROSS-REFERENCE TO RELATED APPLICATIONS

This application claims the benefit of U.S. Provisional Application No. 60/973,374 filed on Sep. 18, 20007, entitled "Ultrasonic Imager for Motion Measurement in Multi-Modality Emission Imaging", which is incorporated herein in its entirety.

TECHNICAL FIELD

The technical field relates to an image reconstruction procedure. More particularly, the system and method relate to an image reconstruction procedure in cardiac and thoracic positron emission tomography (PET), positron emission tomography combined with computed tomography for X-ray (PET/CT), single photon emission computed tomography (SPECT), or single photon emission computed tomography combined with computed tomography for X-ray (SPECT/CT).

BACKGROUND

In cardiac and thoracic PET or PET/CT, the image reconstruction procedure requires a good estimate of the attenuation suffered by pairs of emitted photons. In measuring this and converting the measurements to correction factors, it may be particularly important to account for attenuation edges related to the boundaries between lung and soft tissue, including the moving diaphragm and heart wall. It is axiomatic that one may need to correct the PET data with a different pattern of attenuation correction factors at each moment in time, yet this is not done in normal practice. Instead, one makes do with approximate solutions.

Conventional PET scanners make a transmission measurement lasting several minutes, based on a line source orbiting between the patient and the PET scanner's detectors. In that case, one measures the time-averaged attenuation due to the patient as his chest may have moved through many configurations. Arguably, this may result in a good standard for cardiac PET. In the case of PET/CT, attenuation maps are derived either from the "snapshot" provided by a fast CT scan (to use a metaphor from ordinary photography) or from the "time-exposure" obtained in a slow CT scan. Fast CT scanning of the chest fails to represent faithfully the configuration of attenuating tissue, which is in constant motion. Slow CT somewhat averages organ motions in the chest, but the averaging is not identical to the motion that occurs in a PET scan, which typically lasts for many minutes. Still another approach is the time-averaged CT scan. Of these various approaches, the fast static CT has the advantage of a lower radiation burden.

A need exists to measure the attenuation more accurately to give a better calculation of an emission image. This may improve the quality of the image reconstruction procedure and the resulting image.

Besides the continuous quest for improved image quality, it may be desirable to have an efficient and/or sensitive medical device performing PET, PET/CT, SPECT or SPECT/CT. This would allow for a reduction in time for taking images, an improved quality of the images, and/or a reduction of exposure of a subject to the image apparatus.

Additionally, it is desirable to avoid cumbersome and time consuming arrangements or methods, in an economic and technical perspective, for measuring the attenuation accurately.

SUMMARY

According to an embodiment, a medical imaging device may comprise an emission tomograph, at least one ultrasonic (US) probe for providing images giving real-time information about the location of the internal organs of a subject, a tracking system for spatially locating the at least one ultrasonic probe in relation to the medical imaging device, and an image processing unit in which the location information obtained by the ultrasonic probe is used for attenuation correction of image information obtained by the emission tomograph.

According to a further embodiment, the emission tomograph may be a positron emission tomography (PET) scanner or a single photon emission computed tomography (SPECT) scanner and may further comprise a computed tomography (CT) scanner providing data for basic attenuation correction. According to yet a further embodiment, the emission tomograph may be a PET tomograph further comprising at least one transmission source for basic attenuation correction. According to a further embodiment, the at least one ultrasonic probe may be held against the skin of the thorax of the subject with a belt. According to yet a further embodiment, the medical imaging device may further comprise an US image processing unit for analyzing the real-time information of said ultrasonic probe. According to a further embodiment, the US image processing unit may be operable to detect at least one curve in an image. According to a further embodiment, the US image processing unit may be operable to detect surfaces in an image. According to a further embodiment, at least one warp parameter may be determined by tracking said at least one curve and by tracking said ultrasonic probe and said at least one warp parameter may be used for enhanced attenuation correction. According to a further embodiment, at least one warp parameter may be determined by tracking said at least one surface and by tracking said ultrasonic probe and said at least one warp parameter can be used for enhanced attenuation correction. According to a further embodiment, the means for spatially locating the at least one ultrasonic probe may comprise an optical tracking device that determines the location and orientation of the at least one ultrasonic probe. According to a further embodiment, the means for spatially locating the at least one ultrasonic probe may comprise a mechanical tracking device that determines the location and orientation of the at least one ultrasonic probe. According to a further embodiment, the medical imaging device may further comprise a patient table into which the at least one ultrasonic probe is integrated. According to a further embodiment, the medical imaging device may further comprise an ultrasonic interface arranged between a patient and said ultrasonic probe.

According to another embodiment, a method for measuring attenuation in a subject in a medical imaging device comprising an emission tomograph; at least one ultrasonic probe; and a tracking device for spatially locating the at least one ultrasonic probe, may comprise the steps of: determining basic attenuation for said emission tomograph; determining the location of said ultrasonic probe in relation to the medical imaging system by said tracking device; taking images with the at least one ultrasonic probe; determining at least one warp parameter from said images and said location; and reconstructing a tomograph image of the subject received from said emission tomograph using said basic attenuation and said at least one warp parameter for an enhanced attenuation.

According to a further embodiment, the step of determining at least one warp parameter may comprise the step of detecting at least one curve or surface in an image. According to a further embodiment, the step of determining at least one warp parameter may comprise a sequential analysis of the detected curve or surface over time. According to a further embodiment, the step of determining at least one warp parameter may comprise the step of detecting at least one curve or surface in an image, comparing said curve or surface with an image obtained by a computed tomography system. According to a further embodiment, the method may further comprise the step of iteratively modifying said CT image to match said curve or surface. According to a further embodiment, the method may further comprise the step of determining at least one warp parameter from the iteration. According to a further embodiment, each iterative correction may use types of predefined warping. According to a further embodiment, the types of predefined warping may be determined by at least one of the following factors selected from the group consisting of: — a supine subject's back does not move during the scan; — the diaphragm moves mainly in a superior/inferior direction; — the mediastinum is approximately stationary; and — the top of the lungs are approximately stationary. According to a further embodiment, the method may further comprise the steps of: transforming ultrasonic images at each point in time into at least one curve or surface that defines an organ boundary; determining the warp parameter by transforming at least a partial image including said organ boundary from the emission tomograph into a related warped image whose organ boundaries agree closely with the curve or surface revealed by said ultrasound images. According to a further embodiment, the emission tomograph may be a PET scanner and the method may further comprise the step of: determining said basic attenuation by evaluation of data received by a computed tomography (CT) scanner, wherein attenuation information is transformed at each point in time into attenuation correction factors through the process of converting the image volume of CT numbers (Hounsfield Units, HU) into a 511-keV µ map, forward-projecting the µ map, and forming the exponential of the resulting line integrals. According to a further embodiment, the method may further comprise the steps of: holding the at least one ultrasound probe against the skin of the subject's thorax with a belt; and determining the location and the orientation of the at least one ultrasound probe spatially by means of an optical tracking device. According to a further embodiment, the method may further comprise the step of spatially locating the at least one ultrasonic probe by a mechanical tracking device coupled with said ultrasonic probe that determines the location and orientation of the at least one ultrasonic probe.

According to yet another embodiment, a medical imaging device may comprise a positron emission tomography combined with a computed tomography system (PET/CT) or single photon emission computed tomography combined with a computed tomography system (SPECT/CT), means for determining a basic attenuation correction from data received from said CT system, means for providing ultrasonic images giving real-time information about the location of the internal organs of a subject for determination of an enhanced attenuation correction; and means for spatially locating the ultrasonic images in relation to the medical PET/CT or SPECT/CT tomograph.

According to a further embodiment, the US image processing unit may be operable to detect at least one curve or surfaces in an image. According to a further embodiment, at least one warp parameter may be determined by tracking said at least one curve and by tracking said ultrasonic probe and wherein said at least one warp parameter is used for the enhanced attenuation correction.

Other technical advantages of the present disclosure will be readily apparent to one skilled in the art from the following description and claims. Various embodiments of the present application obtain only a subset of the advantages set forth. No one advantage is critical to the embodiments. Any claimed embodiment may be technically combined with any preceding claimed embodiments).

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain, by way of example, the principles of the invention.

DETAILED DESCRIPTION

The tomography used in the embodiments described herein may involve gathering projection data from multiple directions and feeding the data into a tomographic reconstruction software algorithm processed by a computer. Different types of signal acquisition can be used in similar calculation algorithms in order to create tomographic images by the tomograph. The tomograms may be derived using several different physical phenomena including X-rays, gamma rays, positron-electron annihilation reaction, nuclear magnetic resonance, ultrasound, electrons, and ions. These yield CT, SPECT, PET, magnetic resonance imaging (MRI), ultrasonography, 3D transmission electron microscopy (TEM), and atom probe tomograms, respectively. Additionally, X-rays may be combined with other physical phenomena, for example, PET/CT or SPECT/CT.

PET is a nuclear medicine medical imaging technique which produces a three-dimensional image or map of, for example, functional processes in the body. The system detects pairs of gamma rays emitted indirectly by a positron-emitting radioisotope, which is introduced into the body on a metabolically active molecule. Images of metabolic activity in space are then reconstructed by computer analysis. Scanners may be aided by results from a CT X-ray scan performed at the same time in the same machine.

SPECT is a nuclear medicine tomographic imaging technique using gamma rays. This technique is able to provide true 3D information using a gamma camera. This information is typically presented as cross-sectional slices through, for example, a patient, but can be freely reformatted or manipulated as required. Scanners may be aided by results from a CT X-ray scan performed at the same time in the same machine.

Figure 1A:
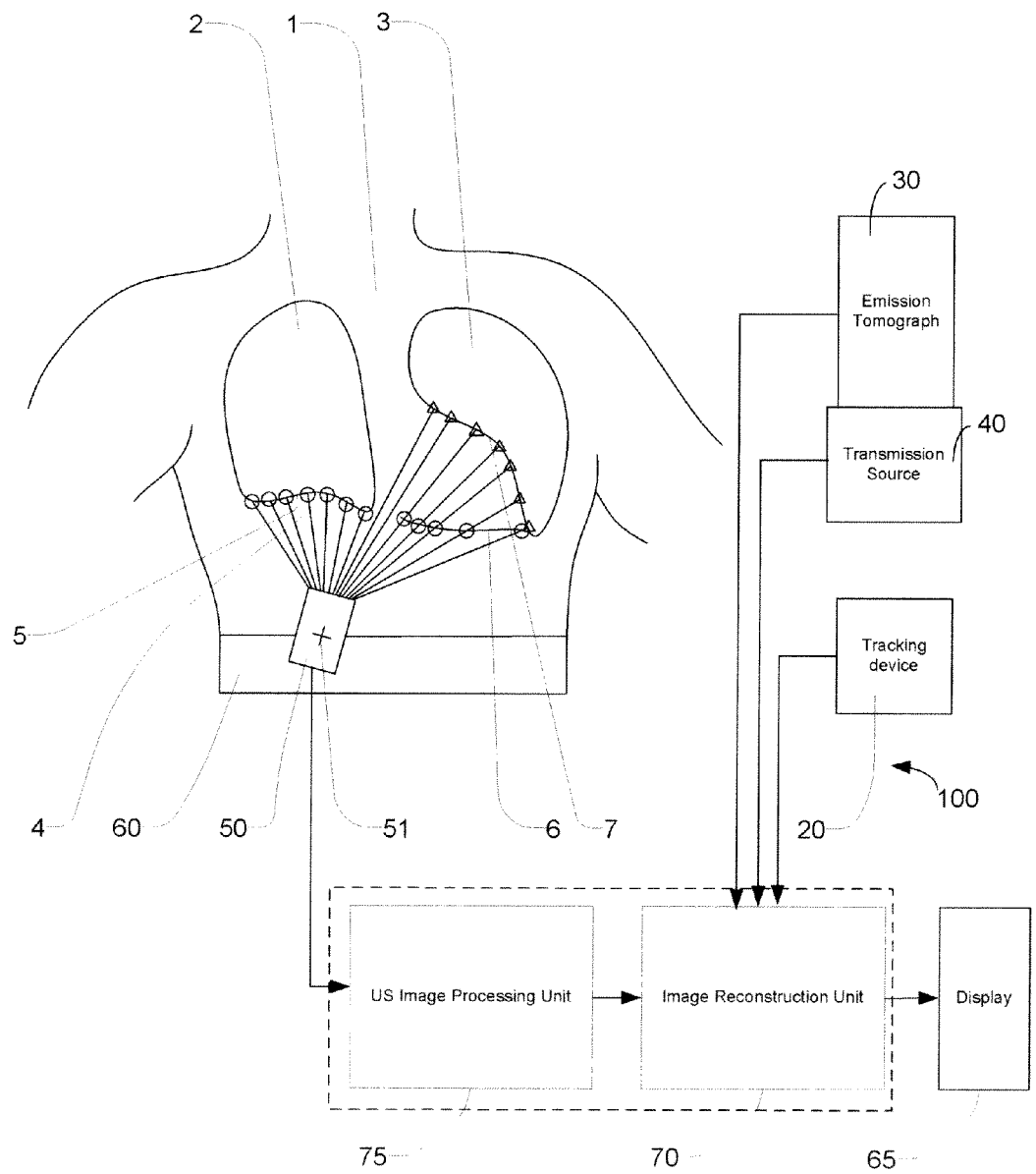
FIG. 1A is an anterior view of a coronal section through a patient in one embodiment using a PET.

FIG. 1A shows an exemplary embodiment of medical imaging device capable of reconstructing images obtained by a PET scan. The embodiment, however, may also apply to any other emission tomography system, for example a SPECT system. FIG. 1A discloses a schematically drawn medical imaging device 100 comprising, for example an emission tomograph 30 such as a PET scanner coupled with an image processing device 70. Coupled to image processing device 70 is a display 65 for displaying data (e.g., images). Furthermore the medical image device may also comprise an attenuation device 40 such as a transmission source for collimating and detecting activity from a radiation source, which provides basic attenuation data for a basic attenuation correction which may then be performed by the image processing device 70. The transmission source 40 may be orbiting the patient along with the emission tomograph 30.

Figure 1B:
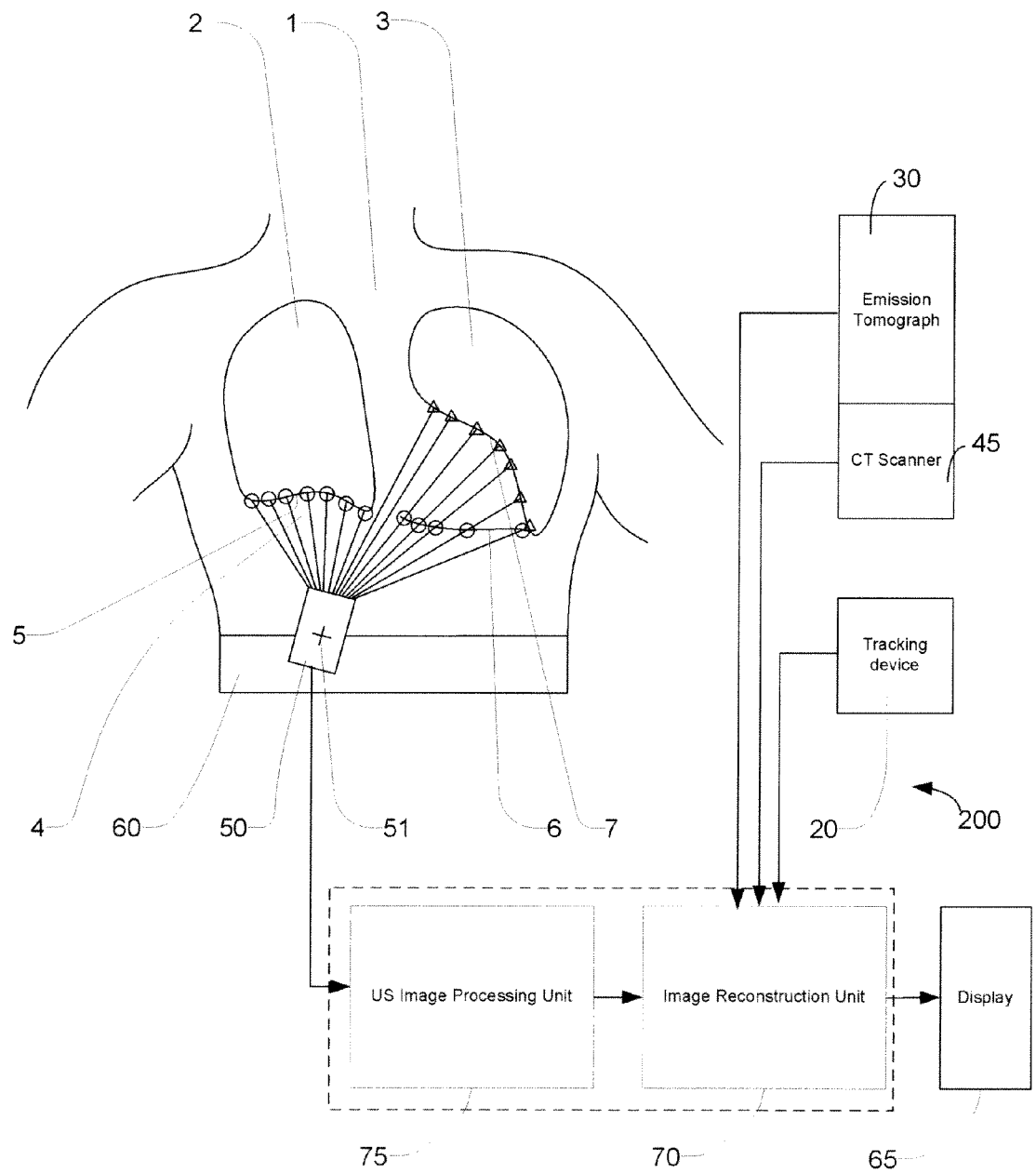
FIG. 1B is an anterior view of a coronal section through a patient in another embodiment using a PET/CT.

FIG. 1B shows another embodiment in form of a medical imaging device 200 capable of reconstructing images obtained by a PET/CT scan. The embodiment, however, may also apply to any other emission tomograph system, for example a SPECT/CT. Similar as FIG. 1A, FIG. 1B discloses a schematically drawn medical imaging device 200 comprising, for example an emission tomograph 30 such as a PET scanner coupled with an image processing/reconstruction device 70. Furthermore the medical image device may also comprise a CT scanner 45 which also provides imaging data that can be evaluated to determine a basic attenuation correction which may then be performed by the image processing/reconstruction device 70. According to various embodiments, FIGS. 1A and 1B show an example of one or more ultrasound (US) imagers (probes) 50 which can be placed near the chest of a subject 1 to allow machine vision of the moving structures within the chest. To this end, the ultrasound imager 50 delivers image data to an US image processing unit 75 at each moment during the PET or PET/CT measurement. The medical imaging device 100 or 200 further comprises tracking means 20 for spatially locating the at least one ultrasound probe 50 in relation to the emission tomograph 30. To this end, the emission tomograph 30, the transmission source 40 or CT scanner 45 may be arranged on the same support structure, for example in a gantry or a support structure orbiting the patient. The probe 50 may comprise a marker 51 such that the tracking means 20, such as for example an optical tracking device, may determine the position and orientation of the at least one ultrasound probe 50.

Figure 1C:
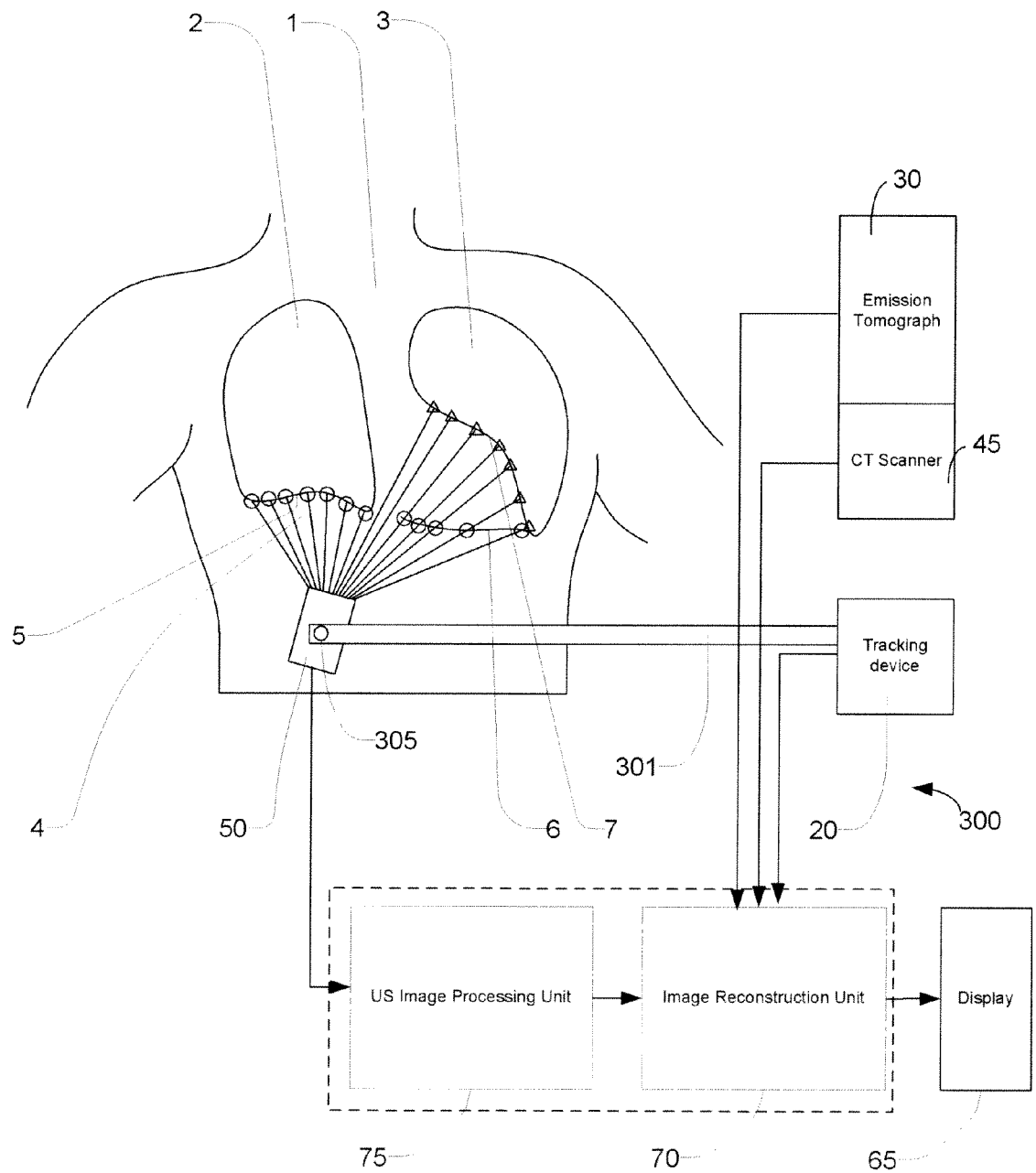
FIG. 1C is an anterior view of a coronal section through a patient in yet another embodiment using a PET/CT.

FIG. 1C shows yet another embodiment of a medical imaging device 300 capable of reconstructing images obtained by a PET/CT scan or other tomograph system. The US probe 50 is mounted on a moveable arm 301 which is coupled with tracking device 20. The moveable arm may have one or a plurality of adjustable joints such as the one indicated by numeral 305 to adjust the position of the US probe 50. According to one embodiment the adjustment joints can be motorized. According to another embodiment, the adjustment joints may be manually manipulated. In either embodiment, sensors are provided which are coupled to the tracking device 20. Thus, tracking device 20 will be able to determine the exact position of the US probe 50 in relation to the position of the tomograph at any time.

Figure 2:
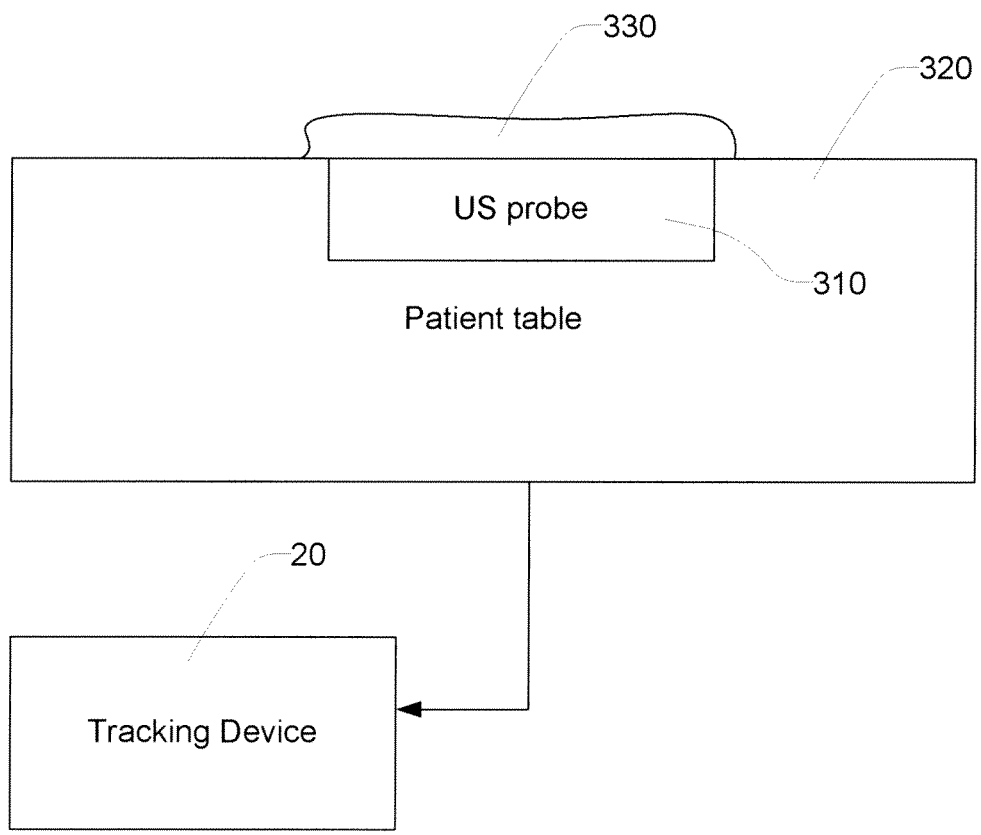
FIG. 2 shows another embodiment of an arrangement of an US probe within a medical device.

FIG. 2 shows yet another embodiment of an arrangement of an US probe within a medical device. In this embodiment, the US probe 310 is integrated within a patient table 320. A patient interface 330 may be arranged on top of the US probe 310. According to one embodiment, this interface 330 may be a cushion filled with a gel such as used with conventional US imaging systems. The interface 330 thus is thus flexible to close any gaps between patient and US probe 310 whenever the patient is placed on the patient table 320. According to other embodiments, the interface 330 may also be implemented as a water bag or equivalent interface in any embodiment that uses a stationary US imaging probe. Other media interfacing between patient and US probe may be used. As shown in FIG. 2, in case of a stationary patient table, the tracking device 20 may track the movement of the tomograph equipment relative to the table. If the tomograph is stationary, then tracking device 20 may be coupled with the patient table 320 or its adjustment mechanism (not shown). Furthermore, if tomograph and patient table are both moveable, then tracking device 20 may be coupled to both and determine the respective difference in movement between the two devices.

The US imager/probe provides for additional information that can be used to perform an enhanced attenuation correction of the emission tomograph. For example, US image processing unit 50, 310 is operable to determine/detect certain curves or surfaces in the images recorded for each moment during the PET or PET/CT measurement. These curves or surfaces may represent for example organ edges or organ surfaces as will be explained in more detail below and will move or distort over time as a subject moves or breathes. Generally, through comparison algorithms sequential US images delivered by the US imager/probe can, for example, be analyzed/compared to images obtained by the CT scanner 45 or attenuation data received from transmission source 40 to determine one or more warp parameters which can be used to enhance the attenuation correction and reconstruct the image obtained by the emission tomograph 30 and/or to correct images of the CT scanner 40 or both. Thus, US image processing unit 75 generates image information forwarded to the image processing/reconstruction unit 70 for an enhanced attenuation correction. Tracking device 20 is used to obtain the location of the US imager 50 with respect to the medical imaging device 10. These tracking data can be used to additionally compensate for any movement of the US probe due to patient movement. These tracking data are also forwarded to image processing/reconstruction unit 70 for determination of the warp parameters. However, a single image processing device may be used instead to perform all image processing. Thus, as indicated by the dotted box, the US image processing/reconstruction unit 75 and the US image processing unit 70 can be realized by a single image processing unit.

FIGS. 1A, 1B and 1C show as an example an anterior view of a coronal section through the subject 1. In this example, the subject's right lung 2 and left lung 3 are shown. Reference numeral 4 marks the area of the liver. Reference numerals 5, 6, and 7 represent internal structures whose location and motion are important in PET attenuation correction and in cardiac emission imaging. They are, for example, the diaphragm, marked by 5 and 6 under the right lung 2 and left lung 3, respectively, and the lateral wall 7 of the heart, respectively.

By placing the ultrasound probe 50 in the suggested location in FIGS. 1A 1B, and 1C or the patient on the respective location of a patient table 320 as shown in FIG. 2, ultrasound radiation may be directed towards the diaphragm 5 and 6 and the heart. Hereby, the edges, marked with circles and triangles in FIG. 1A-C, between soft tissue and the lungs 2 and 3, can be located by the ultrasound probe 50 at every moment during the PET measurement. A human observer can easily see the border between lung and soft tissue, for example liver, heart, blood. In the exemplary embodiment, computer vision techniques applied in US image processing unit 75, for example called edge detection, may be used to identify the edges automatically as indicated with circles and triangles in FIGS. 1A and 1B.

According to an embodiment, the at least one ultrasound probe 50 may be operated in two dimensions, measuring along fan beams. According to another embodiment, the at least one ultrasound probe 50 may also be operated in three dimensions, measuring along cone beams. In the former embodiment with two dimensions, the instrumentation may be comparatively simple and relatively inexpensive. Determination of the location of the edges in each frame of the measurement, at time t, means that US image processing unit 75 identifies curves in space. i.e. determines loci of points $\lambda(t)$, for example the set marked with circles and triangles in FIG. 1. In the latter embodiment, using three dimensions, the instrumentation may be complex and relatively expensive. Location of the edges means that the US image processing unit 75 identifies surfaces in space, i.e. determines loci of points $\sigma(t)$. In other embodiment, surfaces could also be determined by a set of curves. In either embodiment, the significance of finding these edges is that they help the computer determine warp parameters which can be used for the PET and CT processing.

Figure 3:
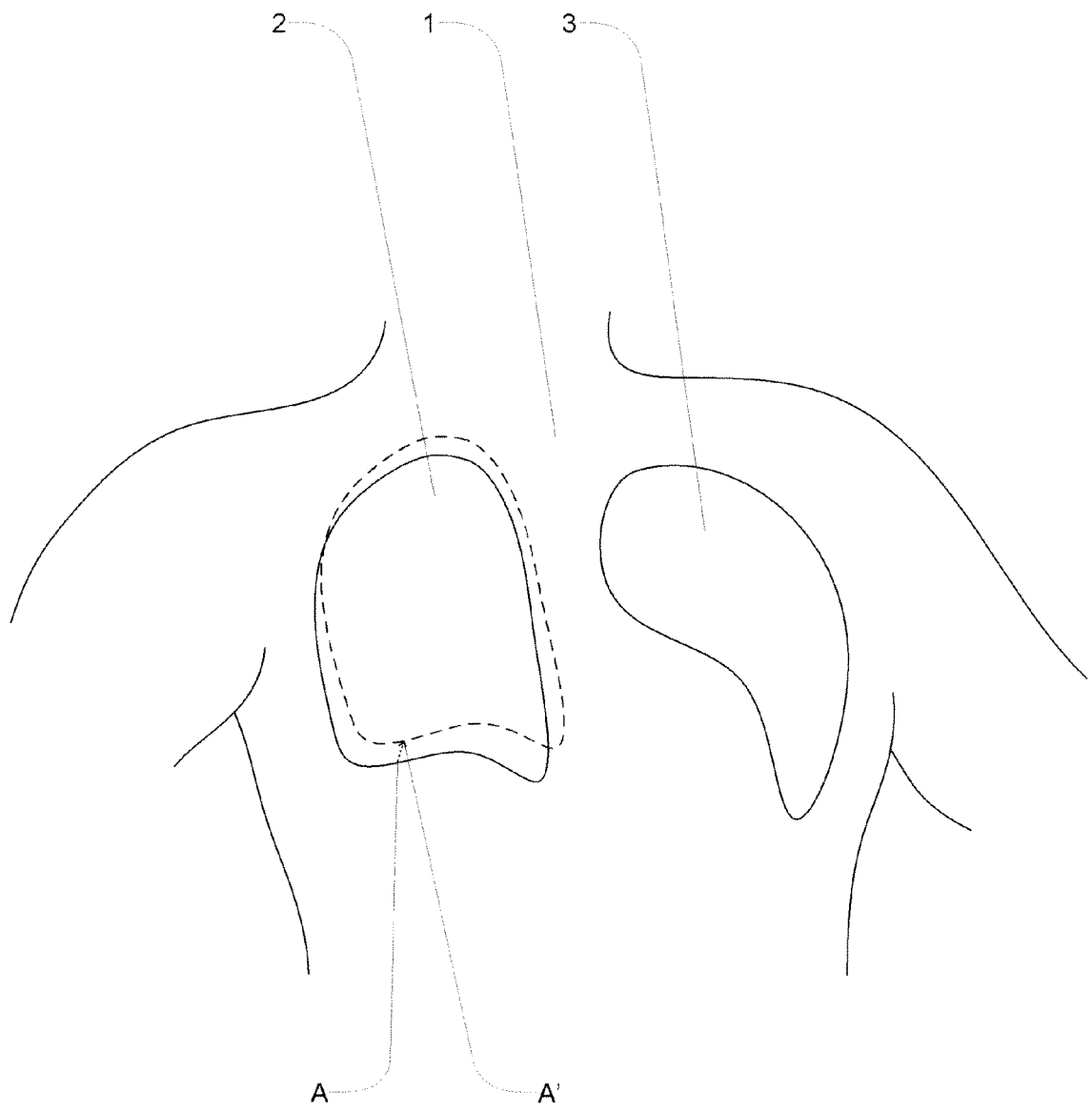
FIG. 3 shows an example of a warping procedure caused by a subject breathing.

The fans' or cones' location and orientation change with the subject's breathing. The curves or surfaces could fall essentially anywhere in three-dimensional space. A warping procedure is shown in FIG. 3. FIG. 3 shows an anterior view of a coronal section through the subject 1. The subject's right lung 2 and left lung 3 are shown.

In the exemplary embodiment shown in FIG. 3, one picture of the anatomy, for example, the one acquired during the CT scan, may be warped into another picture of the anatomy, for example an estimate of the anatomy at a later time. FIG. 3 shows that a given point A on the edge moves to a new location A'. Thus, according to an embodiment, the sequential US probe images can be used to determine certain warp parameters from the change in the shape of the respective curve (or surface).

It may not be practical to use ultrasound to measure the motions of each point in the chest. Therefore, embodiments of the medical device and the method may be aided by assumptions of feasible chest motions. These assumptions may be one or more of the following:

The supine subject's back does not move.
The diaphragm moves mainly in the superior/inferior direction.
The mediastinum does not move.
The tops of the lungs do not move.

Other assumptions may apply. The embodiments described herein do not include a specific model for the motion, because the hardware and the method are general, and because different software algorithms can be used which can give different results. However, at least one adaptive embodiment may rely on the assumption that the space of feasible warps is defined by a small number of parameters, $\{p\}$. For each frame of ultrasound information, the computer may be asked to explore the space of feasible warps, by adjusting those parameters until the curves $\lambda(t)$ or surfaces $\sigma(t)$, determined by the measurement in that frame, agree closely with the model. $\sigma_{model}(\{p\})$ may be the surfaces defined by warp parameters. That is, the measured CT image may be subjected to the specified warp. Edge locations A' in the new space may define the surface $\sigma_{model}(\{p\})$. In the embodiment of two-dimensional ultrasound, let $m(\sigma_{model}, \lambda)$ be a metric defining the distance between $\sigma_{model}$ and the curve $\lambda$. In the embodiment of three-dimensional ultrasound, let $m(\sigma_{model}, \sigma)$ be a metric defining the distance between the surface $\sigma_{model}$ and the surface $\sigma$. In either embodiment, the warp parameters may be adjusted by the computer until the metric is minimized. Let $\{p_0(t)\}$ be the parameters chosen by this procedure, in each frame of the ultrasound measurement. It may then be assumed that the entire three-dimensional space may be warped with the parameters $\{p_0(t)\}$. This procedure leads to the creation, in the computer, of a new μ map for attenuation correction at the time t.

Figure 4:
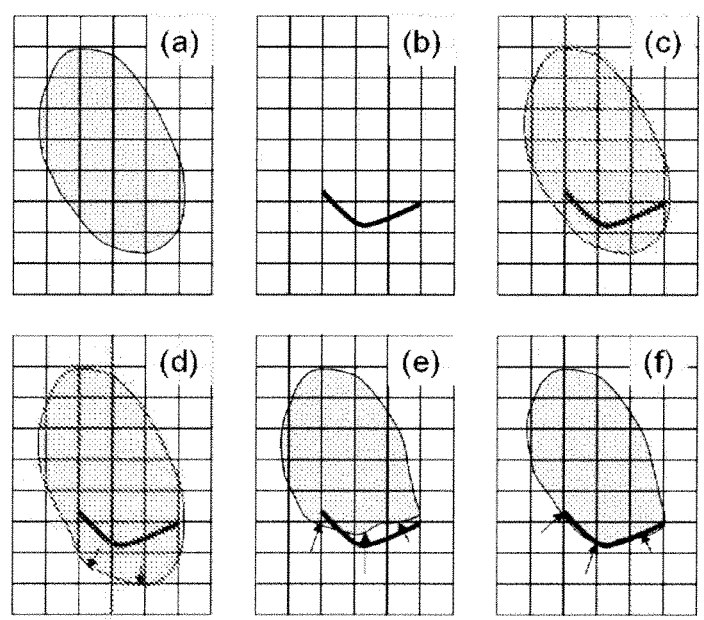
FIG. 4 shows a procedure for attenuation correction according to an embodiment.

The procedure may be illustrated schematically by FIG. 4. Part (a) in FIG. 4 represents an anatomical measurement by, for example, a CT scanner. For example, it could be a measurement revealing the edges of the right or left lung. Part (b) represents an edge determined by ultrasound at a later time. Part (c) shows the overlay of the edge on the anatomy, and shows that the edge is in the wrong place. Part (d) shows that the image can be warped in a way to make the fit even worse. In going from (c) to (d), the metric showing how far the curve is from the CT edge gets larger. Part (e) shows that a different warp can bring the anatomy into better agreement with the edge determined by ultrasound. In this case, the metric is reduced from its initial value, though the fit is still not very good. Part (f) shows that yet another warp can bring the anatomy into close agreement with the measured curve. The metric is brought near to zero in this case, and one may decide that the warp parameters should be applied to the entire volume.

An embodiment comprises means for holding the at least one ultrasound probe 50 tightly against the skin of the subject. A specific means of doing this may be, for example, a belt 60 held under tension. In typical use, a gel would be applied between the at least one ultrasound probe 50 and the skin, as is normal for clinical ultrasound studies.

In order to determine the curves $\lambda(t)$ or surfaces $\sigma(t)$ with accuracy, the location and orientation in space of the ultrasound probe must be known. An embodiment comprises means for making that determination. In this embodiment, an example for knowing the location and orientation in space of the ultrasound probe may comprise an optical tracking system 20. This system 20 may visualize a localizing feature 51 on each of the ultrasound probes. Such a system may be a system as used in medical imaging situations in which motion monitoring may be achieved by digital cameras which take pictures of optical markers placed on a subject, and use machine vision to interpret the images of the markers.

Figure 5:
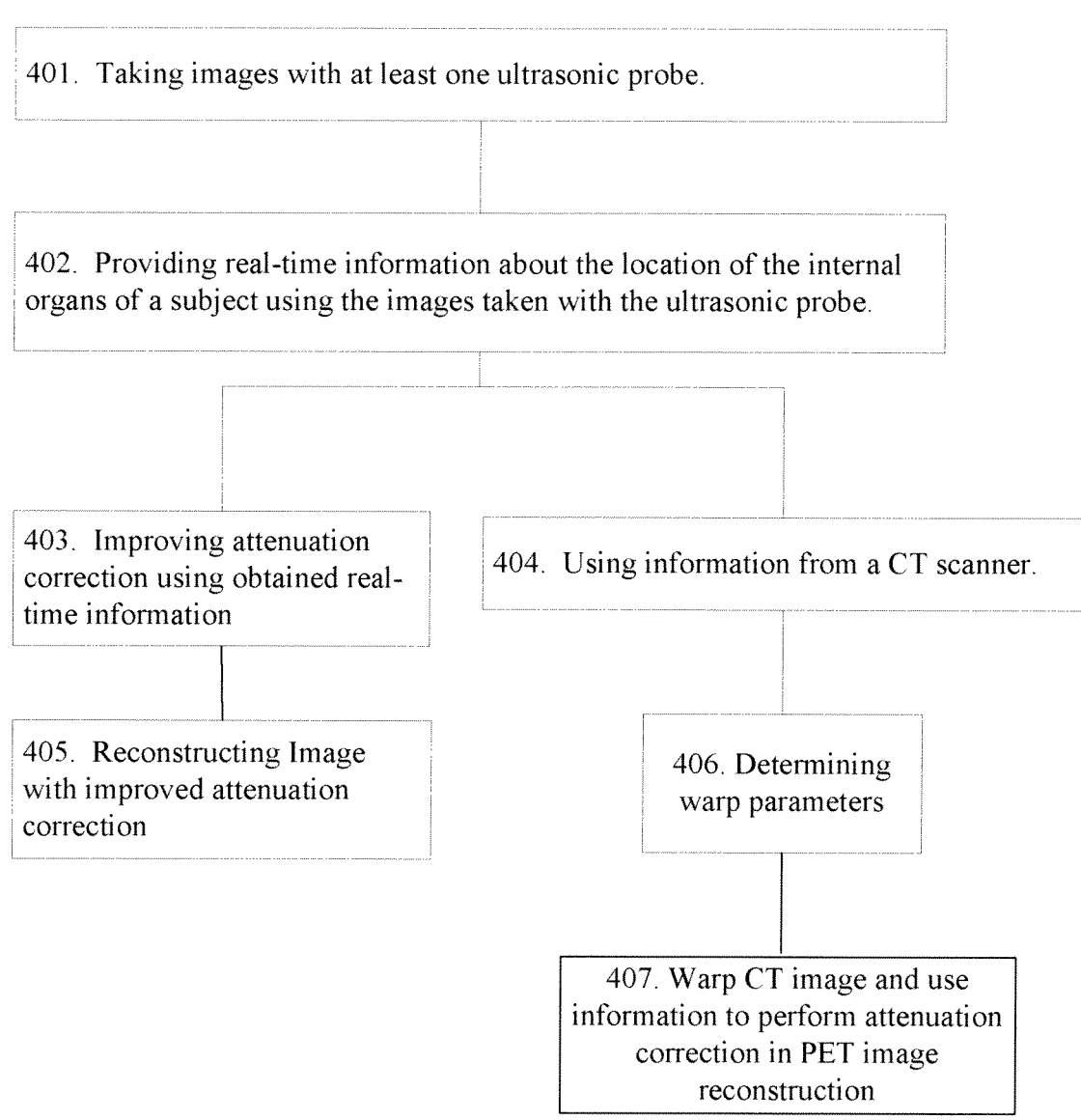
FIG. 5 is a flow chart of the method for attenuation correction according to an embodiment.
Figure 6:
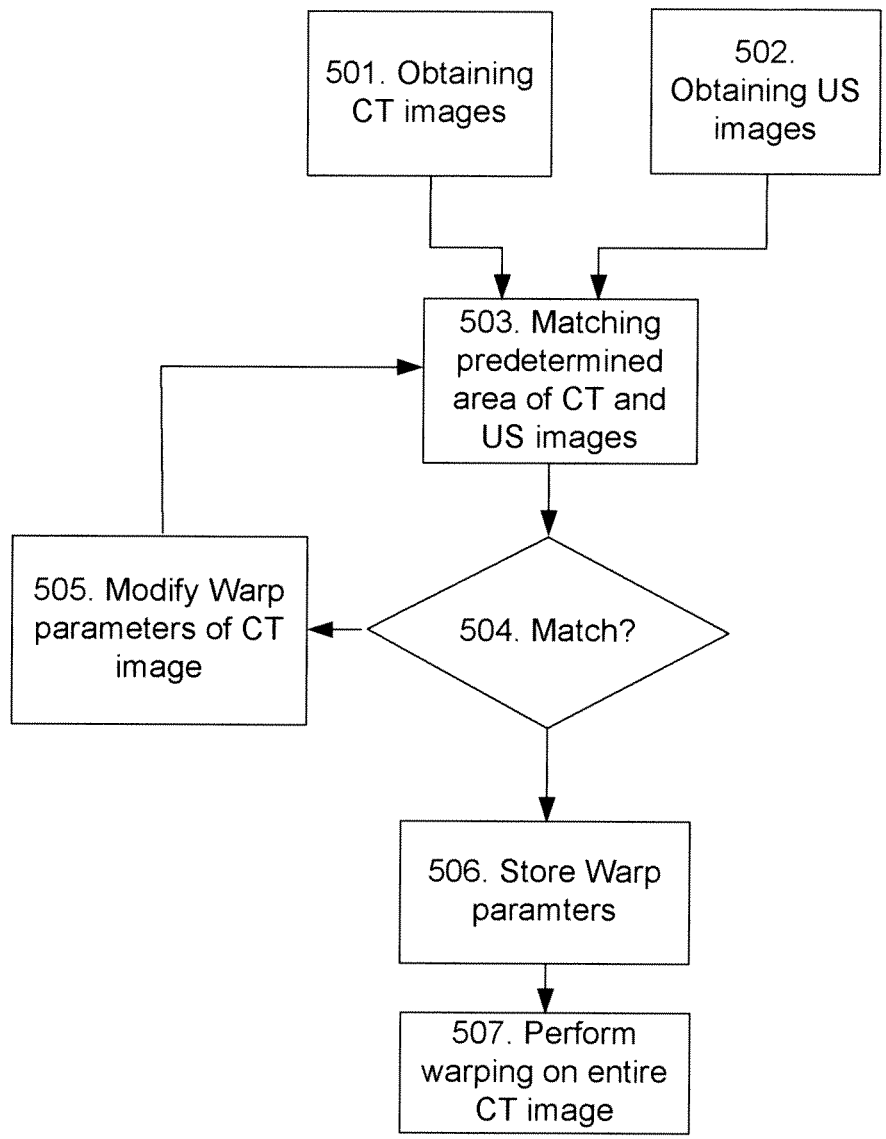
FIG. 6 is a continuation of the flow chart shown in FIG. 5.

FIGS. 5 and 6 show a flow chart of a method for measuring attenuation in a subject in a medical imaging device according to an embodiment. The method may comprise the steps 101 to 108 as outlined in FIGS. 4 and 5.

One exemplary embodiment may be a method for measuring attenuation in a subject in a medical imaging device comprising at least an emission tomograph, at least one ultrasonic probe, and means for spatially locating the at least one ultrasonic probes. In addition, a transmission source may be used to generate rough attenuation data. Moreover, the PET or SPECT may be combined with a CT. The additional attenuation procedure may comprise, according to an embodiment, a first step 401 of taking images with the ultrasonic probe 50. A second step 402 may be providing real-time information, e.g. about the location of the internal organs of the subject, and determination of at least one warp parameters using the images taken with the ultrasonic probe. In a PET or SPECT system, in step 403 the attenuation correction is improved by the real-time information obtained by the US probe 50. In step 405 an image of the subject based on the rough attenuation data and the additional obtained warp parameter is reconstructed. In particular, the warp parameter provides for additional attenuation information over time to compensate for patient and/or organ movements. This exemplary method may measure the attenuation more accurately and at the same time track internal organs to give a better calculation of an emission image. This may improve the image reconstruction procedure and/or image quality.

In a PET/CT or SPECT/CT system, as shown in steps 404-407, the rough attenuation data can be obtained by the CT which provides rough information of body and organ contour as explained in the background. In some embodiments such systems may also comprise a transmission source. However, as explained above, the US probe provides for more accurate warping information which can be used for improving the overall attenuation data and, therefore the reconstruction of the obtained images. Hence, according to an embodiment, in step 404 information from a CT scanner is obtained. In step 406 the warp parameters are determined, for example, by comparison of the CT images and the respective US images obtained at the same time mark or within a predefined time window. In step 407, the CT image is warped according to the determined warp parameters and this information is also used to perform attenuation correction in the PET image reconstruction, ignoring the motion that also occurs in the space of the PET image. However, alternatively, PET images can be reconstructed using the warp parameters.

An embodiment for obtaining the warp parameters in a combined PET/CT or SPECT/CT system is shown in FIG. 6. In steps 501 and 502, CT images and US images are obtained. These images can be obtained at the same time or within predefined time windows to ensure that they are timely correlated. By obtaining these images at the same time it will be ensured that the CT signal fits exactly to the US signal, so there is no need to find the phase of the respiratory cycle in the ultrasound acquisition which matches best to the CT. For the US images, a computer may transform the received ultrasound images at each point in time into a set of spatial edges that define organ boundaries which are anticipated to be attenuating objects. Furthermore, the associated areas in the CT images may be extracted. The respective partial images from the CT and the US probe are then compared in step 503. If no match is detected in step 504, then in step 505 one or more volumetric images from the CT device are transformed or warped according to predefined algorithms. This process is repeated until respective edges or surfaces agree closely with the edges revealed by CT images. Once a close match is determined, the warp parameters will be stored in step 506 and used for performing warping of the entire CT image in step 507.

In a further embodiment, wherein the emission tomograph is a PET scanner, the attenuation information may be transformed at each point in time into attenuation correction factors through the process of converting the image volume of CT numbers (Hounsfield Units) into a 511-keV $\mu$ map, forward-projecting the $\mu$ map, and forming the exponential of the resulting line integrals.

In yet a further embodiment, the at least one ultrasound probe may be held against the skin of the subject's thorax with a belt, and the location and the orientation of the at least one ultrasound probe spatially may be determined by means of an optical tracking device.

Further embodiments may include corrections for the effects of respiratory and cardiac motions and/or taking images two-dimensionally (fans) or three-dimensionally (cones) with the ultrasonic probe.

Even if the above description focuses on PET/CT, the concepts apply without modification to SPECT/CT. However, in an embodiment comprising SPECT the motion may not be likely to repeat from one measurement angle to the next.

The disclosed embodiments have the advantage over conventional methods for obtaining attenuation correction that a low noise image for attenuation correction is obtained by an US probe. Moreover, the additional information about the organ boundaries at each moment during the PET or PET/CT measurement can be used to obtain accurate attenuation correction. This may be performed without any additional dose of ionizing radiation to the patient. The improved attenuation correction method according to various embodiments does not rely on noisy PET measurements and does not assume that a tracer must be present in certain areas in order to work.

The following paragraphs disclose as an example, an embodiment of how additional information can be used to provide for attenuation correction in PET. It is extracted from "Respiratory-gated CT as a tool for the simulation of breathing artifacts in PET and PET/CT," by J. J. Hamill, G. Bosmans, and A. Dekker, Med Phys v. 35 No. 2 (February 2008) p 576-585, in which ten phases of a gated CT study were used to simulate a PET scan in the presence of motion. By presenting this material, the underlying mathematics is explained in the case of two-dimensional sinograms. The somewhat more complicated case of three-dimensional sinograms, used in modern PET scanners, follows a similar prescription. In the study, respiratory gated CT images (GCT) were converted to a map $\mu(\vec{b},r)$ of PET attenuation coefficients at each phase of respiration r and image location $\vec{b}$. These were transformed to a sinogram of attenuation factor values (AF) at each of the ten phases by applying a high-resolution forward projector then rebinned to 168 radial and 168 angular bins, according to the formula $$AF(\vec{d},r)=\exp(-R\{\mu(\vec{b},r)\}). \quad (1)$$

The sinogram of attenuation correction factors (ACF) in each gate is given by $$ACF(\vec{d},r) = \frac{1}{AF(\vec{d},r)}. \quad (2)$$

If the PET volume in each gate r and voxel $\vec{b}$ is denoted O($\vec{b}$,r) then the measured PET data, apart from measurement noise, are expected to be given by sinograms specified by the equation $$p(\vec{d},r)=AF(\vec{d},r) \times R\{O(\vec{b},r)\}(\vec{d},r). \quad (3)$$

The PET image is obtained by multiplying this by the sinogram of attenuation correction factors, according to the equation $$I(\vec{b},r)=R^{-1}\{p(\vec{d},r) \times ACF(\vec{d},r)\}. \quad (4)$$

where $R^{-1}$ is the inverse Radon transformation. This image represents the object at each phase of respiration with negligible distortions due to motion. The images in each individual gate r are accurate but will be affected by image noise, as always happens in PET. In case this noise prevents easy reading of the images, a less noisy image can be realized by warping the images into a common frame of reference and adding the image voxel values.

The medical imaging device and method discussed above measures the attenuation more accurately, at the same time as tracking some of the internal organs to give a better calculation of an emission image. Embodiments of the invention, therefore, are well adapted to carry out the objects and attain the ends and advantages mentioned, as well as others inherent therein. While the disclosure has been described and is defined by reference to particular preferred embodiments of the invention, such references do not imply a limitation, and no such limitation is to be inferred. Embodiments of the invention are capable of considerable modification, alteration, and equivalents in form and function, as will occur to those ordinarily skilled in the pertinent arts. The described preferred embodiments are exemplary only, and are not exhaustive. Consequently, the disclosure is intended to be limited only by the spirit and scope of the appended claims, giving full cognizance to equivalents in all respects.

What is claimed is:

1. A medical imaging device comprising:
an emission tomograph configured to obtain an emission image of a subject;
a transmission source configured to obtain a transmission image of said subject;
at least one ultrasonic (US) probe adapted to provide US images giving real-time location information of internal organs of said subject wherein said real-time location information comprises a loci of points ($\sigma(t)$);
a tracking system adapted to spatially locate the at least one ultrasonic probe in relation to other imaging modalities of the medical imaging device;
a US image processing unit adapted to compare real-time location information from said US probe with transmission image information previously obtained from said transmission source, wherein said real-time location information is time-correlated with emission image information from said emission tomograph, and to determine at least one warp parameter indicating a locational difference between an anatomical feature in said previously obtained transmission image and said real-time location information, wherein said determination further uses tracking information from said tracking system; and
an image processing unit in which the warp parameter obtained by the US image processing unit is used to modify attenuation correction of emission image information time-correlated with said real-time location information.

2. The medical imaging device according to claim 1, wherein the emission tomograph is one of a positron emission tomography (PET) scanner and a single photon emission computed tomography (SPECT) scanner, and wherein said transmission source comprises a CT scanner providing data for basic attenuation correction.

3. The medical imaging device according to claim 1, wherein the emission tomograph is a PET tomograph, and said transmission source is used for obtaining basic attenuation correction information.

4. The medical imaging device according to claim 1, wherein the at least one ultrasonic probe is held against thorax skin of the subject with a belt.

5. The medical imaging device according to claim 1, wherein said US image processing unit analyzes the real-time information of said ultrasonic probe.

6. The medical imaging device according to claim 1, wherein said at least one warp parameter is used for enhanced attenuation correction.

7. The medical imaging device according to claim 1, wherein the tracking system for spatially locating the at least one ultrasonic probe comprises an optical tracking device that determines a location and orientation of the at least one ultrasonic probe.

8. The medical imaging device according to claim 1, wherein the tracking system for spatially locating the at least one ultrasonic probe comprises a mechanical tracking device that determines a location and orientation of the at least one ultrasonic probe.

9. The medical imaging device according to claim 1, further comprising a patient table into which the at least one ultrasonic probe is integrated.

10. The medical imaging device according to claim 9, further comprising an ultrasonic interface arranged between a patient and said ultrasonic probe.

11. A method for correcting emission image information of a subject for attenuation comprising:
determining basic attenuation correction information for said subject from transmission image information of said subject obtained from a transmission source;
obtaining ultrasonic (US) image information of said subject obtained from an ultrasonic source, that is time-correlated with corresponding emission image information obtained from said subject;
comparing, by an image processing unit, said US image information with said transmission image information used to determine said basic attenuation correction information;
calculating, by said image processing unit, a warp parameter corresponding to a locational difference between an anatomical feature in said transmission image information and said US image information;
using said warp parameter to modify said basic attenuation correction information for emission image information time-correlated with said US image information; and
reconstructing, in said image processing unit, a tomograph image of the subject from said emission image information using said modified attenuation correction information.

12. The method according to claim 11, further comprising:
transforming, by said image processing unit, an ultrasonic image at a point in time correlated with a corresponding emission image, into at least one curve or surface that defines an organ boundary; and
calculating, by said image processing unit, the warp parameter by transforming at least a partial image including said organ boundary from the transmission image into a related warped image whose organ boundaries agree closely with the curve or surface revealed by said ultrasound images.

13. The method according to claim 12, wherein the emission image information is obtained from a PET scanner and the method further comprises:
determining said basic attenuation correction information by evaluation of data received by a CT scanner, wherein said basic attenuation correction information is transformed at a point in time into attenuation correction factors through a process of converting an image volume of CT numbers into a 511-keV $\mu$ map, forward-projecting the 511-keV $\mu$ map, and forming an exponential of resulting line integrals.

14. The method according to claim 11, further comprising:
using an ultrasonic probe to obtain said US image information;
holding said ultrasonic probe against thorax skin of the subject with a belt;
determining the location and an orientation of said ultrasonic probe spatially using an optical tracking device; and
using the determined location and spatial orientation in the calculation of said warp parameter.

15. The method according to claim 11, further comprising using an ultrasonic probe to obtain said US image information, spatially locating the ultrasonic probe by a mechanical tracking device coupled with said ultrasonic probe that determines the location and an orientation of the ultrasonic probe.

16. A medical imaging device comprising:
- a combined positron emission tomography-computed tomography system (PET/CT) or combined single photon emission computed tomography-computed tomography system (SPECT/CT);
- an ultrasonic (US) image processing unit configured to determine basic attenuation correction data for a subject from transmission data of said subject received from said CT system;
- an image processing unit configured to provide ultrasonic images of said subject giving real-time location information for determination of enhanced attenuation correction data, wherein said real-time location information comprises a loci of points ($\sigma(t)$), wherein said real-time location information is time-correlated with corresponding emission data of said subject from said PET or SPECT system;
- said ultrasonic (US) image processing unit configured to compare said real-time location information with corresponding information from said transmission data used to determine said basic attenuation correction data, and to determine a warp parameter indicative of a locational difference between said real-time location information and said transmission data used to determine said basic attenuation correction data; and
- said image processing unit configured to reconstruct an emission image from emission data of said PET or SPECT system using enhanced attenuation correction data obtained by modifying said basic attenuation correction data using said warp parameter.

* * * * *